(12) United States Patent
Lee-Huang et al.

(10) Patent No.: US 7,838,275 B2
(45) Date of Patent: Nov. 23, 2010

(54) ANTI-HIV AND ANTI-TUMOR PEPTIDES AND FRAGMENTS OF LYSOZYME

(75) Inventors: Sylvia Lee-Huang, New York, NY (US); Philip L. Huang, Maple Glen, PA (US); Paul Huang, Boston, MA (US)

(73) Assignee: New York University, New York, NY (US)

( * ) Notice: Subject to any disclaimer, the term of this patent is extended or adjusted under 35 U.S.C. 154(b) by 550 days.

(21) Appl. No.: 10/487,259

(22) PCT Filed: Jul. 9, 2001

(86) PCT No.: PCT/US01/21582
§ 371 (c)(1),
(2), (4) Date: Aug. 31, 2004

(87) PCT Pub. No.: WO02/04011
PCT Pub. Date: Jan. 17, 2002

(65) Prior Publication Data
US 2005/0008631 A1    Jan. 13, 2005

Related U.S. Application Data

(60) Provisional application No. 60/216,702, filed on Jul. 7, 2000.

(51) Int. Cl.
*C12N 9/36* (2006.01)
*A61K 38/47* (2006.01)
(52) U.S. Cl. .......... 435/206; 424/94.61; 424/188.1; 424/94.6; 424/94.1; 435/200; 435/195; 435/183
(58) Field of Classification Search .......... 424/94.61, 424/94.6, 94.1, 188.1; 435/206, 200, 195, 435/183
See application file for complete search history.

(56) References Cited

U.S. PATENT DOCUMENTS 5,554,501 A     9/1996  Coassin
5,583,211 A *  12/1996  Coassin et al. .......... 536/23.1
5,919,639 A     7/1999  Humphreys et al.

FOREIGN PATENT DOCUMENTS

| JP | 06-211692 | * | 8/1994 |
|---|---|---|---|
| WO | WO 95/09176 A1 | | 4/1995 |
| WO | WO 95/11912 A2 | | 5/1995 |
| WO | WO 98/26747 A2 | | 6/1998 |
| WO | WO 00/57920 A2 | | 10/2000 |

OTHER PUBLICATIONS

Laible et al. Bactericidal activity of human lysozyme, muramidase-inactive lysozyme, and cationic polypeptides against *Streptococcus sanguis* and *Streptococcus faecalis*: inhibition by chitin oligosaccharides. Infect Immun. Jun. 1985;48(3):720-8.*
Burkitt. 1999 Treatment Briefs: Pregnant Women's Urine Analyzed for Antiviral Agents. Treatment Issues: Newsletter of Experimental AIDS Therapies—vol. 13, No. 3.*
Huang et al. 2000 Identification, characterization and synthesis of lysozyme mimetics with potent anti-HIV activity.*
NCBI sequence viewer for lysozyme (http://www.ncbi.nlm.nih.gov/entrez/viewer.fcgi?db=protein&val=1335210).*
NCBI sequence viewer for lysozyme precursor, http://www.ncbi.nlm.nih.gov/entrez/viewer.fcgi?db=protein&val=4557894.*
Chen. HC 2005 Structure and function of peptide and protein hormones (NICHD, NIH Annual report 2005) (http://eclipse.nichd.nih.gov/nichd/annualreport/2005/errb/umspc.htm).*
Pellegrini et al. 1997 Identification and isolation of a bactericidal domain in chicken egg white lysozyme. J. Appl. Microbiol. 82:372-378. Abstract only.*
Gait and Karn. Progress in anti-HIV structure-based drug design. TIBTECH. 1995. vol. 13, pp. 430-438.*
Perrin and Telenti. HIV Treatment Failure: Testing for HIV Resistance in Clinical Practice. Science vol. 280. Jun. 19, 1998. p. 1871-1873.*
Yarchoan and Broder. Correlations between the in vitro and in vivo activity of anti-HIV agents: implications for future drug development. J. Enzyme Inhibition. 1992. vol. 6, pp. 99-111.*

* cited by examiner

*Primary Examiner*—Taeyoon Kim
(74) *Attorney, Agent, or Firm*—Browdy and Neimark, PLLC

(57) ABSTRACT

A fragment of lysozyme which contains a minimum nine amino acid sequence with antiviral, anti-tumor and bactericidal activities but lacking muramidase activity is provided. The invention also relates to pharmaceutical compositions containing this fragment and methods for treating HIV infection or for inhibiting tumor growth using this fragment as an active ingredient.

8 Claims, No Drawings

SEQUENCE LISTING

```
<160> NUMBER OF SEQ ID NOS: 14

<210> SEQ ID NO 1
<211> LENGTH: 18
<212> TYPE: PRT
<213> ORGANISM: Homo sapiens

<400> SEQUENCE: 1

Arg Val Val Arg Asp Pro Gln Gly Ile Arg Ala Trp Val Ala Trp Arg
1               5                   10                  15

Asn Arg
```

<210> SEQ ID NO 2
<211> LENGTH: 18
<212> TYPE: PRT
<213> ORGANISM: Artificial Sequence
<220> FEATURE:
<223> OTHER INFORMATION: Synthetic

<400> SEQUENCE: 2

Arg Val Val Arg Asp Pro Gln Gly Ile Arg Ala Tyr Val Ala Trp Arg
1               5                   10                  15

Asn Arg

<210> SEQ ID NO 3
<211> LENGTH: 18
<212> TYPE: PRT
<213> ORGANISM: Artificial Sequence
<220> FEATURE:
<223> OTHER INFORMATION: Synthetic

<400> SEQUENCE: 3

Arg Val Val Arg Asp Pro Gln Gly Ile Arg Ala Trp Val Ala Tyr Arg
1               5                   10                  15

Asn Arg

<210> SEQ ID NO 4
<211> LENGTH: 18
<212> TYPE: PRT
<213> ORGANISM: Artificial Sequence
<220> FEATURE:
<223> OTHER INFORMATION: Synthetic

<400> SEQUENCE: 4

Arg Val Val Arg Asp Pro Gln Gly Ile Asn Ala Trp Val Ala Trp Arg
1               5                   10                  15

Asn Arg

<210> SEQ ID NO 5
<211> LENGTH: 18
<212> TYPE: PRT
<213> ORGANISM: Artificial Sequence
<220> FEATURE:
<223> OTHER INFORMATION: Synthetic

<400> SEQUENCE: 5

Arg Val Val Arg Asp Pro Gln Gly Ile Arg Ala Trp Val Ala Trp Lys
1               5                   10                  15

Asn Arg

<210> SEQ ID NO 6
<211> LENGTH: 18
<212> TYPE: PRT
<213> ORGANISM: Artificial Sequence
<220> FEATURE:
<223> OTHER INFORMATION: Synthetic

<400> SEQUENCE: 6

Arg Val Val Arg Asp Pro Gln Gly Ile Arg Ala Trp Val Ala Trp Arg
1               5                   10                  15

Asn Lys

<210> SEQ ID NO 7
<211> LENGTH: 9

```
<212> TYPE: PRT
<213> ORGANISM: Homo sapiens

<400> SEQUENCE: 7

Arg Val Val Arg Asp Pro Gln Gly Ile
1               5

<210> SEQ ID NO 8
<211> LENGTH: 9
<212> TYPE: PRT
<213> ORGANISM: Homo sapiens

<400> SEQUENCE: 8

Arg Ala Trp Val Ala Trp Arg Asn Arg
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic

<400> SEQUENCE: 9

Ala Trp Arg Trp Arg Ala Arg Val Asn
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic

<400> SEQUENCE: 10

Arg Ala Tyr Val Ala Trp Arg Asn Arg
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic

<400> SEQUENCE: 11

Arg Ala Trp Val Ala Tyr Arg Asn Arg
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic

<400> SEQUENCE: 12

Asn Ala Trp Val Ala Trp Arg Asn Arg
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic
```

-continued

```
<400> SEQUENCE: 13

Arg Ala Trp Val Ala Trp Lys Asn Arg
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic

<400> SEQUENCE: 14

Arg Ala Trp Val Ala Trp Arg Asn Lys
1               5
```

ANTI-HIV AND ANTI-TUMOR PEPTIDES AND FRAGMENTS OF LYSOZYME

GOVERNMENT LICENSE RIGHTS

The experiments performed in this application were supported in part by the National Institute of Allergy and Infectious Diseases, grant no. ROI AI-31343. The U.S. Government may have a paid up license in this invention and may have the right in limited circumstances to require the patent owner to license others on reasonable terms as provided by the terms of the above grant.

BACKGROUND OF THE INVENTION

1. Field of the Invention

The present invention relates to anti-viral and anti-tumor peptides and polypeptides.

2. Description of the Related Art

The transmission of HIV type 1 (HIV-1) from mother to fetus is rare during the first trimester of pregnancy when the secretion of human chorionic gonadotropin (hCG) is high in the placenta (De Rossi et al., 1992; Krivine et al., 1995). It was found that the β-subunit of hCG (hCGβ), but not the α-subunit, is active against HIV-1 virus (Bourinbaiar et al., 1995) and AIDS-related Kaposi's sarcoma (Lunardi-Iskandar et al., 1995) in AIDS patients (Gill et al., 1996) and HIV-1 transgenic mice (De et al., 1997). These studies were conducted by using heterogeneous commercial preparations with different potencies reported for different source materials. There has been controversy as to whether the activity against Kaposi's sarcoma found in hCGP preparations is caused by hCGβ itself or other proteins (Griffiths et al., 1997; DeMarchi et al., 1997; Hopp et al., 1997; Flamand et al., 1998). Recently the present inventors reported their discovery that lysozyme contributes to the antiviral (anti-HIV-1) and anti-HHV8 activity of the β-core preparations of hCG.

Lysozymes are a family of enzymes that are widespread in nature. Hen egg-white lysozyme is a classic representative of this enzyme family, and the related enzymes found in birds and many other animals, such as mammals, reptiles and invertebrates are designated as chicken-type (c-type or conventional-type) lysozymes. Lysozyme was sequenced in the early 1960s and it was the first enzyme for which a complete X-ray crystallographic analysis was performed. All lysozymes have bactericidal activity and they all have muramidase activity which cleaves a β-glycosidic band between the C-1 of N-acetylmuramic acid and the C-4 of N-acetylglucosamine of peptidoglycan. The reference text, Lysozyme: Model Enzymes in *Biochemistry and Biology*, ed. P. Jolles, Birkhauser Verlag, Basel, Switzerland, 1996, provides a review of this family of enzymes. FIG. 1 on pages 10-11 of this text provides an alignment of the amino acid sequences of lysozymes from various organisms. In human lysozyme, the active site for muramidase activity resides in the cleft formed around residues Glu35 and Asp52.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a fragment of lysozyme which contains what was discovered by the present inventors to be the minimum nine amino acid sequence (SEQ ID NO:8) required to retain the full antiviral and anti-tumor activities of lysozyme. This fragment of lysozyme further lacks muramidase activity.

The present invention also provides a pharmaceutical composition containing the fragment of lysozyme according to the present invention and a pharmaceutically acceptable diluent, excipient, carrier or auxiliary agent.

Further provided by the present invention are a method for treating viral and bacterial infections, such as HIV infection, and a method for inhibiting tumor growth by administering to a subject in need thereof the fragment of lysozyme according to the present invention.

DETAILED DESCRIPTION OF THE INVENTION

The present inventors have now delineated the minimum fragment of human lysozyme, which is a small nine amino acid residue fragment of SEQ ID NO:8 corresponding to residues 107-115 of human lysozyme, required for retaining full antiviral activity of full-length lysozyme. Surprisingly, this small nine amino acid fragment also retained the anti-tumor activity and bactericidal activity associated with full-length human lysozyme.

According to the present invention, a fragment of lysozyme is provided which has antiviral, anti-tumor and bactericidal activities but lacks the muramidase activity of lysozyme. This fragment of lysozyme contains the nine amino acid residues of SEQ ID NO:8 and consists of preferably 9 to 50 amino acid residues, more preferably 9 to 30 amino acid residues, and most preferably 9 to 18 amino acid residues. When the fragment of lysozyme consists of 9 amino acid residues, it has the amino acid sequence of SEQ ID NO:8. A second embodiment of the fragment of lysozyme according to the present invention consists of the amino acid sequence of SEQ ID NO:1.

It is preferred that when an amino acid sequence(s) flanks the nine residue sequence of SEQ ID NO:8 on either or both sides, such flanking sequence(s) retains the α-helical conformation of native human lysozyme in the region immediately surrounding residues 107-115.

Also encompassed by the present invention is a variant of a fragment of native mammalian lysozyme, such as human lysozyme, where one to five amino acid substitutions, deletions or additions are present in the sequences flanking the amino acid sequence of SEQ ID NO:8. Amino acid substitutions in these flanking sequences are preferably, though not limited to, conservative substitutions as would be well understood by those of skill in the art. Such variants all contain the amino acid sequence of SEQ ID NO:8 and retain the antiviral, anti-tumor and bactericidal activities of full length native human lysozyme.

The present invention also comprehends chemical derivatives and salts of the fragment of lysozyme according to the present invention, which retain the antiviral, anti-tumor and bactericidal activities of lysozyme. A "chemical derivative" contains additional chemical moieties not normally part of the lysozyme amino acid sequence. Covalent modifications of the amino acid sequence are included within the scope of this invention. Such modifications may be introduced into the fragment of lysozyme by reacting targeted amino acid residues of the fragment with an organic derivatizing agent that is capable of reacting with selected side chains or terminal residues.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, alpha-bromo-beta-(5-imidazoyl)propionic acid, chloroacetyl phosphate, N-alkylmaleimides, 3-nitro-2-pyridyl disulfide, methyl-2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Parabromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino acid-containing residues include imidoesters, such as methyl picolinimidate, pyridoxal phosphate, pyridoxal, chloroborohydride, trinitrobenzenesulfonic acid, O-methyliosurea, 2,4-pentanedione, and transaminase-catalyzed reaction with glyoxylate.

Arginyl residues are modified by reaction with one or several conventional reagents, among them phenylglyoxal, 2,3-butanedione, and ninhydrin. Derivatization of arginine residues requires that the reaction be performed in alkaline conditions because of the high pKa of the guanidine functional group. Furthermore, these reagents may react with the groups of lysine, as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidazole and tetranitromethane are used to form O-acetyl tyrosyl species and e-nitro derivatives, respectively.

Carboxyl side groups (aspartyl or glutamyl) are selectively modified by reaction with carbodiimides (R'N—C—N—R') such as 1-cyclohexyl-3-[2-morpholinyl-(4-ethyl)]carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful for cross-linking the fragment of lysozyme to a water-insoluble support matrix or to other macromolecular carriers. Commonly used cross-linking agents include, e.g., 1,1-bis(diazoacetyl)-2-phenylethane, glutaraldehyde, N-hydroxysuccinimide esters, for example, ester with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizating agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (Creighton, 1983), acetylation of the N-terminal amine, and, in some instances, amidation of the C-terminal carboxyl groups.

Such derivatized moieties may improve the solubility, absorption, biological half life, and the like. The moieties may alternatively eliminate or attenuate any undesirable side effect of the fragment and the like. Moieties capable of mediating such effects are disclosed, for example, in *Remington's Pharmaceutical Sciences*, 16th ed., Mack Publishing Co., Easton, Pa. (1980).

Another aspect of the present invention makes use of the antiviral, anti-tumor and bactericidal properties of the fragment of lysozyme according to the present invention. The fragment of lysozyme can be administered to a subject in need thereof to treat a viral infection, such as HIV infection, or a bacterial infection, or the fragment can be administered to inhibit tumor growth.

The fragment of lysozyme according to the present invention may be administered by any means that achieves its intended purpose. For example, administration may be by a number of different parenteral routes including, but not limited to, subcutaneous, intravenous, intradermal, intramuscular, intraperitoneal, intracerebral, intranasal, oral, transdermal, or buccal routes. Parenteral administration can be bolus injection or by gradual perfusion over time.

It is understood that the dosage administered will be dependent upon the age, sex, health, and weight of the recipient, kind of concurrent treatment, if any, frequency of treatment, and the nature of the effect desired. The total dose required for each treatment may be administered by multiple doses or in a single dose. By "effective amount", it is meant a concentration of the fragment of lysozyme which is capable of inhibiting or reducing viral or bacterial infection or is capable of inhibiting tumor growth. Such concentrations can be routinely determined by those of skill in the art. It will also be appreciated by those of skill in the art that the dosage may be dependent on the stability of the administered fragment. A less stable fragment may require administration in multiple doses.

Preparations for parenteral administration include sterile aqueous or non-aqueous solutions, suspensions, and emulsions, which may contain diluents, excipients, or auxiliary agents which are known in the art. Pharmaceutical compositions such as tablets and capsules can also be prepared according to routine methods.

Pharmaceutical compositions comprising the fragment of lysozyme according to the present invention include all compositions wherein the fragment is contained in an amount effective to achieve its intended purpose. In addition, the pharmaceutical compositions may contain suitable pharmaceutically acceptable carriers comprising excipients and auxiliaries which facilitate processing of the active compounds into preparations which can be used pharmaceutically. Suitable pharmaceutically acceptable vehicles are well known in the art and are described for example in Gennaro, Alfonso, Ed., *Remington's Pharmaceutical Sciences*, 18th Edition 1990, Mack Publishing Co., Easton, Pa., a standard reference text in this field. Pharmaceutically acceptable vehicles can be routinely selected in accordance with the mode of administration and the solubility and stability of the fragment of lysozyme. For example, formulations for intravenous administration may include sterile aqueous solutions which may also contain buffers, diluents and other suitable additives.

Suitable formulations for parenteral administration include aqueous solutions of the active compounds in water-soluble form, for example, water-soluble salts. In addition, suspension of the active compound as appropriate oily injection suspensions may be administered. Suitable lipophilic solvents or vehicles include fatty oils, for example, sesame oil, or synthetic fatty acid esters for example ethyl oleate or triglycerides. Aqueous injection suspensions that may contain substances which increase the viscosity of the suspension include, for example, sodium carboxymethyl cellulose, sorbitol, and/or dextran. Optionally, the suspension may also contain stabilizers.

Having now generally described the invention, the same will be more readily understood through reference to the following example which is provided by way of illustration and is not intended to be limiting of the present invention.

EXAMPLE

Clostripain Digestion of Human Lysozyme

Human lysozyme (2 mg) was treated with clostripain (10 units, Sigma) in 400 µl of Tris buffer, pH7.6 at 37° C. for 24 h. The digest was resolved by reversed phase chromatography on a ProRPC column (Hr5/10). A total of 10 peptide fragments were identified. The fractions were assayed for anti-HIV activity by p24 production in HIV-1 infected ACH2 T lymphocytes as described in Lee-Huang et al. (1999). The bulk of anti-HIV activity was found in peak 7. Peak 6 contained about 10-15% of the anti-HIV activity present in peak 7, and peak 8 contained only trace amounts of anti-HIV activity. Peaks 8-10 represent trace undigested material.

Peak 7 fractions were pooled and re-purified by reversed phase chromatography on a ProRPC (Hr5/5) column using acetonitrile gradient elution. A major peak was obtained. Anti-HIV activity was found in the major peak that was eluted at 30-36% acetonitrile. This region consists of 18 amino acids (SEQ ID NO:1), corresponding to residues 98-115 of human lysozyme. It is designated HL18. The anti-HIV $EC_{50}$ (50% inhibition concentration) of HL18 is 58 nM whereas that of the intact lysozyme is 55 nM, indicating that they are comparable and within the same order of magnitude (Table 1). This is the first identification and isolation of an anti-HIV peptide from lysozyme.

TABLE 1

Molecular Modeling of the Anti-HIV activity of HL18

| Peptides | Sequence (N→C) | Anti-HIV activity (EC50) |
|---|---|---|
| Lysozyme | Whole molecule | 50 nM |
| HL18 (Peak 7) | RVVRDPQGIRAWVAWRNR (SEQ ID NO: 1) | 56 nM |
| HL18 (Synthetic) | RVVRDPQGIRAWVAWRNR (SEQ ID NO: 1) | 58 Nm |
| HL18 (W109-Y) | RVVRDPQGIRAYVAWRNR (SEQ ID NO: 2) | No Anti-HIV Activity |
| HL18 (W112-Y) | RVVRDPQGIRAWVAYRNR (SEQ ID NO: 3) | No Anti-HIV Activity |
| HL18 (R107-N) | RVVRDPQGINAWVAWRNR (SEQ ID NO: 4) | >100 mM |
| HL18 (R113-K) | RVVRDPQGIRAWVAWKNR (SEQ ID NO: 5) | >100 mM |
| HL18 (R115-K) | RVVRDPQGIRAWVAWRNK (SEQ ID NO: 6) | >100 mM |
| HL18-N9 (N-term-9) | RVVRDPQGI (SEQ ID NO: 7) | No Anti-HIV Activity |
| HL18-C9 (C-term-9) | RAWVAWRNR (SEQ ID NO: 8) | 55 nM |

Molecular Modeling of Lysozyme Fragments

In order to gain insight into the role of specific amino acids for the anti-HIV activity in HL18, molecular modeling was carried out. To test the relative importance of charge and hydrophobicity for anti-HIV activity, single amino acid substitution was conducted. Substitution of tryptophan 109 or 112 by the less hydrophobic tryrosine resulted in complete loss of anti-HIV activity. Substitution of the positively charged Arginine at positions 107, 113, or 115 with Aspargine or lysine resulted in the reduction of antiviral activity (Table 1). These results suggest that both the hydrophobic amino acid tryptophan and the positively charged arginine residues are critical for the anti-HIV activity of HL18. These residues are located in the C-terminal half of the peptide HL18. To define the precise sequence of HL18 responsible for the anti-HIV activity, two peptide fragments were synthesized and tested for anti-HIV activity. Peptide HL18-N9 corresponds to the N-terminal 9 amino acids of HL18. It consists of the amino acid sequence of SEQ ID NO:7. Peptide HL9 (HL18-C9) consists of the amino acid sequence of (SEQ ID NO:8) and represents the C-terminal half of HL18 (R107-R115). HLN9 demonstrated no anti-HIV activity whereas HL9 exhibited full anti-HIV activity with an EC50 of about 55 nM, comparable to that of HL 18 and the intact lysozyme. The same amino acid substitutions discussed above for HL18 were made in HL9 and the anti-HIV activities were found to be the comparable (Table 2).

TABLE 2

Molecular Modeling of the Anti-HIV activity of HL18

| Peptides | Sequence (N→C) | Anti-HIV activity (EC50) |
|---|---|---|
| Lysozyme | Whole molecule | 50 nM |
| HL18 | RVVRDPQGIRAWVAWRNR (SEQ ID NO: 1) | 56 Nm |
| HL9 (HL18-C9) | RAWVAWRNR (SEQ ID NO: 8) | 55 nM |
| HL9 (Scrambled) | AWRWRARVN (SEQ ID NO: 9) | No Anti-HIV Activity |
| HL9 (W109→Y) | RAYVAWRNR (SEQ ID NO: 10) | No Anti-HIV Activity |
| HL9 (W112→Y) | RAWVAYRNR (SEQ ID NO: 11) | No Anti-HIV Activity |
| HL9 (R107→N) | NAWVAWRNR (SEQ ID NO: 12) | >100 µM |
| HL9 (R113→K) | RAWVAWKNR (SEQ ID NO: 13) | >100 µM |
| HL9 (R115→K) | RAWVAWRNK (SEQ ID NO: 14) | >100 µM |

Table 3 shows that the anti-HIV activity of HL9 is potent against a wide spectrum of HIV-1, including primary isolates, laboratory strains and resistant strains with EC50 of 55-68 nM. Table 4 shows the bioactivities of the lysozyme fragments, where it can be seen that no toxicity was observed in the dose range of the assay, and HL18 and HL9 inhibits the proliferation of HHV8 infected cells of AIDS patients with Kaposi's sarcoma but lack muramidase activity.

TABLE 3

Anti-HIV Activity of HL9 with Different Strains

| HIV-1 | Inhibition on p24 Expression EC50 (Nm) |
|---|---|
| HTLV-IIIB | 55 |
| HIV-1Ada-M | 58 |
| HIV-174.MT2 | 52 |
| HIV-1 302054 | 68 |

TABLE 4

Bioactivities of Lysozyme Fragments

| Compounds | Anti-HIV EC50 nM | Anti-KS EC50 nM | Bactericidal Activity | Muramidase Activity | Toxicity |
|---|---|---|---|---|---|
| Lysozyme | 50 | 54 | +++ | +++ | — |
| HL18 | 58 | 56 | +++ | — | — |
| HL9 | 55 | 48 | +++ | — | — |
| HL9 (W to Y) | — | — | — | — | — |
| HL9 (R to K) | >100 µM | >200 µM | — | — | — |
| HL9 (S) | — | — | — | — | — |

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Albini et al., The beta-core fragment of human chorionic gonadotrophin inhibits growth of Kaposi's sarcoma-derived cells and a new immortalized Kaposi's sarcoma cell line *AIDS* 11:713-721 (1997)

Bourinbaiar et al., Anti-HIV effect of beta subunit of human chorionic gonadotropin (beta hCG) in vitro *Immunol. Lett.* (1995)

De et al., Human chorionic gonadotropin hormone prevents wasting syndrome and death in HIV-1 transgenic mice *J. Clin. Invest.* 99:1484-1491 (1997)

De Rossi et al., Vertical transmission of HIV-1: lack of detectable virus in peripheral blood cells of infected children at birth *AIDS* 6:1117-1120 (1992)

Flamand et al., Effects of a urinary factor from women in early pregnancy on HIV-1, SIV and associated disease *Nat. Med.* 4:428-434 (1998)

Gill et al., The effects of preparations of human chorionic gonadotropin on AIDS-related Kaposils sarcoma *N. Engl. J. Med.* 335:1261-1269 (1996)

Griffiths et al., Ribonuclease inhibits Kaposi's sarcoma *Nature* 390:568

Hopp, *Nat. Biotech.* 12:834-835 (1997)

Jolles, P. (ed.), *Lysozyme: Model Enzymes in Biochemistry and Biology*, Birkhauser Verlag, Basel, Switzerland, (1996)

Krivine et al., HIV replication during the first weeks of life *Lancet* 339:187-1189 (1992)

Lee-Huang et al., Lysozyme and RNases as anti-HIV components in β-core preparations of human chorionic gonadotropin, *Proc. Natl. Acad. Sci. USA* 96:2678-2681 (1999)

Lunardi-Iskandar et al., Tumorigenesis and metastasis of neoplastic Kaposi's sarcoma cell line in immunodeficient mice blocked by a human pregnancy hormone *Nature* 375:64-68 (1995)

What is claimed is:

1. A method for inhibiting HIV infection in cells in vitro or growth of Kaposi's sarcoma cells in vitro, comprising providing to said cells an effective amount of a 9-50 amino acid long fragment of lysozyme with anti-HIV activity or Kaposi's sarcoma-inhibiting activity but lacking muramidase activity, which fragment comprises the amino acid sequence SEQ ID NO:8.

2. A method according to claim 1, for inhibiting said HIV infection in cells in vitro.

3. The method of claim 1 for inhibiting said growth of Kaposi's sarcoma cells in vitro.

4. The method of claim 1, wherein the length of the fragment is 9 to 18 amino acid residues.

5. The method of claim 4, wherein the sequence of the fragment is:
   (a) SEQ ID NO:1; or
   (b) SEQ ID NO:8.

6. The method of claim 5, wherein the sequence of the fragment is SEQ ID NO:8.

7. The method of claim 1, wherein a sequence flanking SEQ ID NO:8 retains the α-helical conformation of regions that flank SEQ ID NO:8 in native human lysozyme.

8. The method of claim 1, wherein a sequence flanking SEQ ID NO:8, has one to five amino acid substitutions or deletions compared to native human lysozyme sequence in such flanking amino acid residues.

* * * * *